US006449335B1

(12) United States Patent
Siochi (10) Patent No.: US 6,449,335 B1
(45) Date of Patent: *Sep. 10, 2002

(54) SYSTEM AND METHOD FOR OPTIMIZING RADIATION TREATMENT WITH AN INTENSITY MODULATING MULTI-LEAF COLLIMATOR

(75) Inventor: Ramon Alfredo Carvalho Siochi, Apex, NC (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 36 days.

This patent is subject to a terminal disclaimer.

(21) Appl. No.: 09/649,285

(22) Filed: Aug. 23, 2000

(51) Int. Cl.[7] .................................................. A61N 5/10

(52) U.S. Cl. ........................................ 378/65; 378/147

(58) Field of Search ......................... 378/65, 147, 150, 378/108

(56) References Cited

U.S. PATENT DOCUMENTS

| | | | |
|---|---|---|---|
| 5,663,999 A | | 9/1997 | Siochi .......................... 378/65 |
| 5,724,403 A | | 3/1998 | Siochi et al. ................ 378/150 |
| 5,726,400 A | * | 3/1998 | Swerloff et al. .............. 378/65 |
| 6,052,436 A | * | 4/2000 | Huttner et al. ............... 378/152 |
| 6,188,748 B1 | * | 2/2001 | Pastyr et al. ................. 378/151 |
| 6,240,161 B1 | * | 5/2001 | Siochi .......................... 378/65 |
| 6,240,162 B1 | * | 5/2001 | Hernandez-Guerra et al. ... 378/65 |
| 6,260,999 B1 | * | 7/2001 | Wofford et al. .............. 378/205 |

OTHER PUBLICATIONS

Bortfield T, Kaler DL, Waldron TJ, et al. "X-ray Field Compensation with Multileaf Collimators," Int J. Radiation Oncology Biol Phys 1994;28:723-730.

Spirous SV, Chui CS.. "Generation of Arbitrary Intensity Profiles by Dynamic Jaws or Multileaf Collimators," Medical Physics 1994;21:1031-1041.

Svensson R., Kallman P., Brahme A. "An Analytical Solution for the Dynamic Control of Multileaf Collimators" Phys Med Biol 1994;39:37-61.

Van Santvoort JPC, Heijmen BJM. "Dynamic Multileaf Collimation Without 'Tongue-and-Groove' Underdosage Effects," Phys Med Biol 1996;41:2091-2105.

Convery Dj, Rosenbloom ME. "The Generation of Intensity-Modulated Fields for Conformal Radiotherapy by Dynamic Collimation," Phys Med Biol. 1992;37:1359-1374.

R.A.C. Siochi, "Minimizing Static Intensity Modulation Delivery Time Using an Intensity Solid Paradigm," Int. J. Radiation Oncology Biol, Phys. 43,671-680 (1999).

Galvin JM Chen XG, Smith Rm, "Combining Multileaf Fields to Modulate Fluence Distributins," Int. J. Radiation, Oncology Biol Phys1993;27 697-705.

* cited by examiner

*Primary Examiner*—Robert H. Kim
*Assistant Examiner*—Irakli Kiknadze (57) ABSTRACT

A method for sequencing treatment fields defined by leaves of a multi-leaf collimator positioned to block radiation from a radiation source and define an opening between the radiation source and a treatment area. The multi-leaf collimator is operable to rotate relative to the treatment area to define a plurality of treatment ports. Each of the ports has at least one treatment field. The method includes ordering the collimator ports based on direction of travel of the collimator relative to the treatment area such that each port has at least one corresponding adjacent port. The method further includes selecting a sequence of treatment fields for each collimator port based on the treatment fields within adjacent ports to optimize delivery of radiation.

15 Claims, 6 Drawing Sheets

SYSTEM AND METHOD FOR OPTIMIZING RADIATION TREATMENT WITH AN INTENSITY MODULATING MULTI-LEAF COLLIMATOR

FIELD OF THE INVENTION

The present invention relates generally to a radiation emitting device, and more particularly, to a system and method for efficiently delivering radiation treatment.

BACKGROUND OF THE INVENTION

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located within the gantry for generating a high energy radiation beam for therapy. This high energy radiation beam may be an electron beam or photon (x-ray) beam, for example. During treatment, the radiation beam is trained on a zone of a patient lying in the isocenter of the gantry rotation.

In order to control the radiation emitted toward the patient, a beam shielding device, such as a plate arrangement or collimator, is typically provided in the trajectory of the radiation beam between the radiation source and the patient. An example of a plate arrangement is a set of four plates which can be used to define an opening for the radiation beam. The collimator is a beam shielding device which may include multiple leaves (e.g., relatively thin plates or rods) typically arranged as opposing leaf pairs. The plates are formed of a relatively dense and radiation impervious material and are generally independently positionable to delimit the radiation beam.

The beam shielding device defines a field on the zone of the patient for which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the healthy organs surrounding and overlying the tumor limits the dosage that can be delivered to the tumor.

The delivery of radiation by a radiation therapy device is typically prescribed by an oncologist. The prescription is a definition of a particular volume and level of radiation permitted to be delivered to that volume. Actual operation of the radiation equipment, however, is normally done by a therapist. The radiation emitting device is programmed to deliver the specific treatment prescribed by the oncologist. When programming the device for treatment, the therapist has to take into account the actual radiation output and has to adjust the dose delivery based on the plate arrangement opening to achieve the prescribed radiation treatment at the desired depth in the target.

The radiation therapist's challenge is to determine the best number of fields and intensity levels to optimize dose volume histograms, which define a cumulative level of radiation that is to be delivered to a specified volume. Typical optimization engines optimize the dose volume histograms by considering the oncologist's prescription, or three-dimensional specification of the dosage to be delivered. In such optimization engines, the three-dimensional volume is broken into cells, each cell defining a particular level of radiation to be administered. The outputs of the optimization engines are intensity maps, which are determined by varying the intensity at each cell in the map. The intensity maps specify a number of fields defining optimized intensity levels at each cell. The fields may be statically or dynamically modulated, such that a different accumulated dosage is received at different points in the field. Once radiation has been delivered according to the intensity map, the accumulated dosage at each cell, or dose volume histogram, should correspond to the prescription as closely as possible.

In such intensity modulation radiation treatments, multiple fields are often used to deliver radiation to a treatment area. The different intensity fields may involve different locations (i.e., ports) of the multi-leaf collimator relative to the treatment area or different shaped fields created by repositioning leaves of the multi-leaf collimator. The sequence of the treatment fields within each port is typically randomly chosen with no attention given to the sequence that occurs in going from one port to the next and how the step between ports affects the sequencing within a port. The segments are often arranged to travel from left to right within a port, without regard to leaf positions within adjacent ports. Thus, when the collimator moves to a new port, the leaves are already positioned to the right from the last treatment field for the previous port and the leaves must travel back to the left before starting delivery of the first treatment field at the next port. This sequencing of treatment fields results in unnecessary leaf travel, thus, increasing treatment time and wear on the leaves and equipment.

Accordingly, there is therefore, a need for a method and system for optimizing radiation treatment with a multi-leaf collimator to increase the life of the collimator or reduce treatment time.

SUMMARY OF THE INVENTION

A method and system for optimizing radiation delivery with a multi-leaf collimator are disclosed.

A method of the present invention is for sequencing treatment fields defined by leaves of a multi-leaf collimator positioned to block radiation from a radiation source and define an opening between the radiation source and a treatment area. The multi-leaf collimator is operable to rotate relative to the treatment area to define a plurality of treatment ports, each port having one or more treatment fields. The method generally comprises ordering the collimator ports based on direction of travel of the collimator relative to the treatment area such that each port has at least one corresponding adjacent port and selecting a sequence of treatment fields for each collimator port based on the treatment fields within adjacent ports to optimize delivery of radiation.

In another aspect of the invention, the treatment fields for each of the ports are configured to treat generally the same region within the treatment area. The method generally includes ordering the collimator ports based on direction of travel of the collimator relative to the treatment area such that each port has at least one adjacent port and selecting a sequence of the treatment fields for each collimator port such that the leaves are moved from one treatment field to the next within a port in opposite longitudinal directions for adjacent ports to optimize delivery of radiation.

The radiation treatment may be optimized to reduce total radiation treatment time or reduce the overall leaf travel between treatment fields. The treatment fields may be sequenced independently for each port. The order of the treatment fields within each port may then be modified based on the position of leaves for the last treatment field of the previous port or the first treatment field of a subsequent port. Alternatively, the treatment fields may be sequenced for a first collimator port and the first treatment field for the second port selected based on the leaf positions of the last treatment field for the first port. The sequence of treatment fields for the second port is then optimized based on the first treatment field. This process is continued until the sequence of treatment fields for each port is selected.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

The following description is presented to enable one of ordinary skill in the art to make and use the invention and is provided in the context of a patent application and its requirements. Various modifications to the preferred embodiments will be readily apparent to those skilled in the art and the generic principles herein may be applied to other embodiments. Thus, the present invention is not intended to be limited to the embodiment shown but is to be accorded the widest scope consistent with the principles and features described herein.

Figure 1:
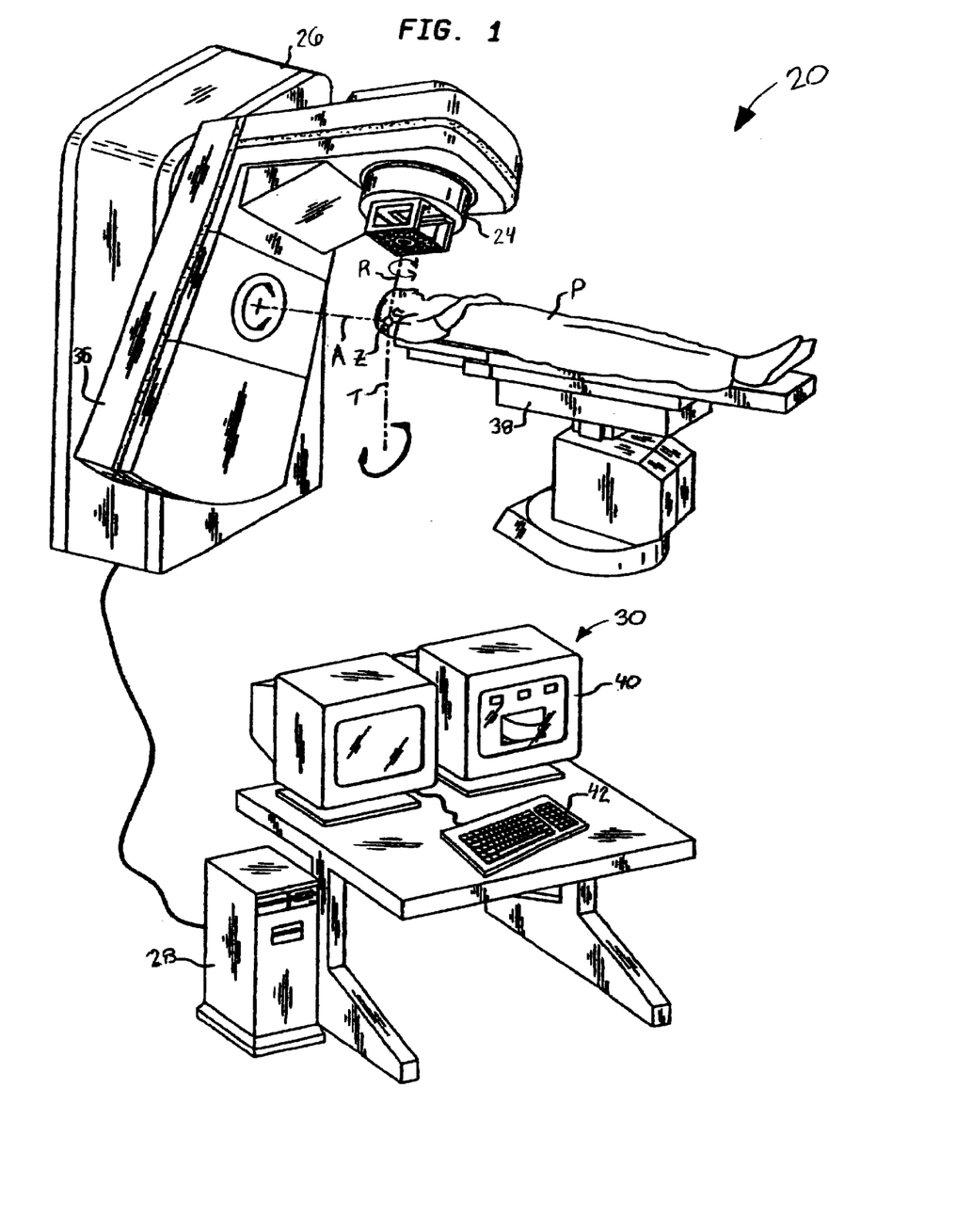
FIG. 1 is a diagram of a radiation treatment device and treatment console according to an embodiment of the present invention and a patient positioned for treatment within the treatment device.

Referring now to the drawings, and first to FIG. 1, a radiation treatment device of the present invention is shown and generally indicated at 20. The radiation treatment device 20 includes a beam shielding device (not shown) within a treatment head 24, a control unit within a housing 26 connected to a treatment processing unit, generally indicated at 30. The radiation treatment device further includes a gantry 36 which can be swiveled for rotation about axis A in the course of a therapeutic treatment. The treatment head 24 is fixed to the gantry 36 for movement therewith and a linear accelerator is located within the gantry for generating high powered radiation used for therapy. The radiation emitted from the linear accelerator extends generally along axis R. Electron, photon, or any other detectable radiation may be used for the therapy. During treatment, the radiation beam is focused on a zone Z of an object P (e.g., a patient who is to be treated). The zone to be treated is located at an isocenter defined by the intersection of the rotational axis A of the gantry 36, rotational axis T of treatment table 38, and the radiation beam axis R. The rotatable gantry 36 allows for different beam angles and radiation distributions without having to move the patient.

The treatment processing unit 30 is used to input information, such as radiation intensity and location of treatment, into the radiation treatment device 20 and output data for monitoring of the treatment. The processing unit 30 includes an output device such as a visual display monitor 40 and an input device such as a keyboard 42. The treatment processing unit 30 is typically operated by a therapist who administers actual delivery of radiation treatment as prescribed by an oncologist. The therapist uses the keyboard 42 to enter data, which defines the radiation dose to be delivered to the patient, into the processing unit 30. The data may also be input via other input devices, such as a data storage device, for example. Various types of data can be displayed before and during the treatment on the screen of the display monitor 40.

Figure 2:
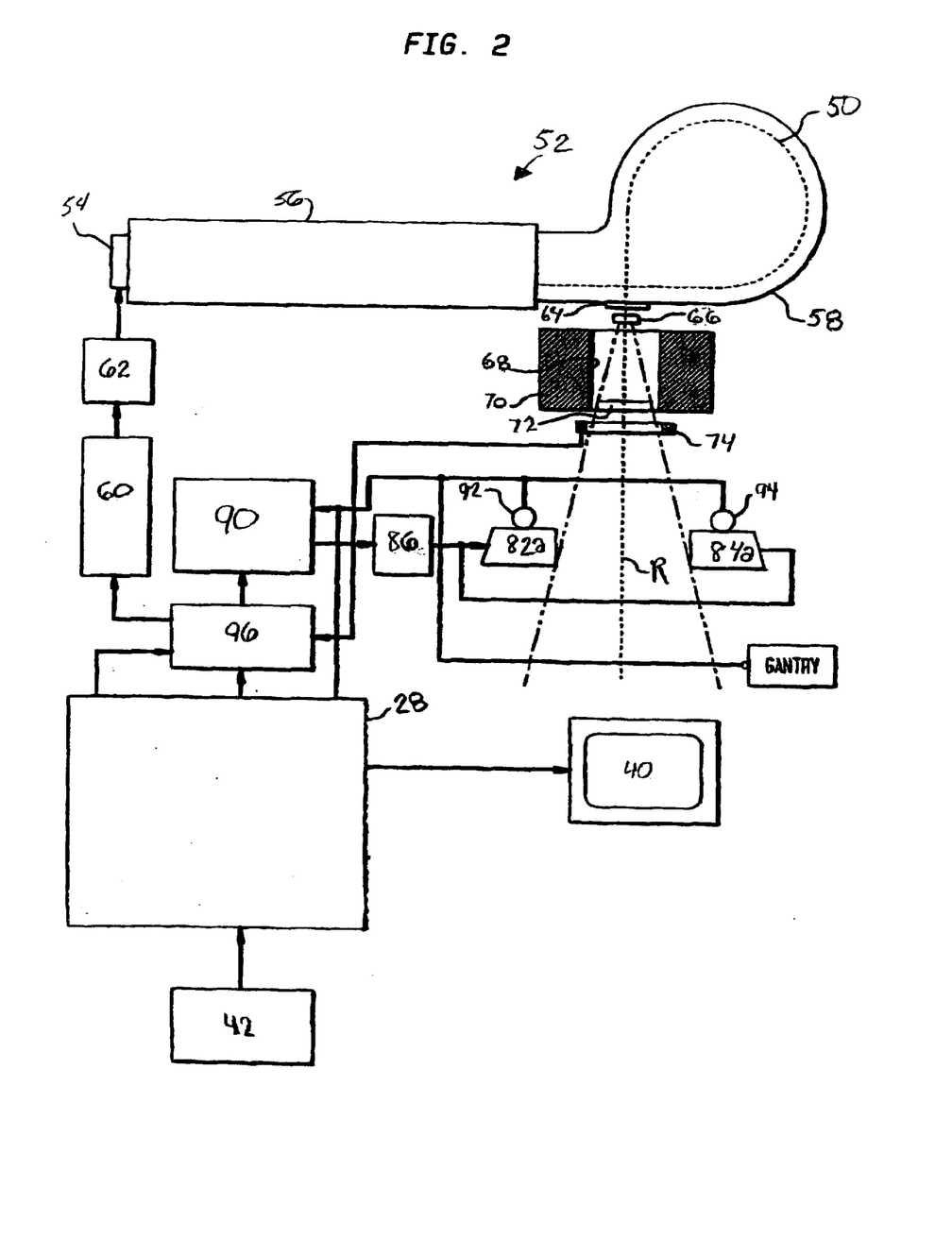
FIG. 2 is a block diagram illustrating portions of the radiation treatment device of FIG. 1.

FIG. 2 is a block diagram of the radiation treatment device 20 showing portions of the treatment processing unit 30 in further detail. An electron beam 50 is generated in an electron accelerator, generally indicated at 52. The electron accelerator 52 includes an electron gun 54, wave guide 56, and an evacuated envelope or guide magnet 58. A trigger system 60 generates injector trigger signals and supplies them to an injector 62. Based on these injector trigger signals, the injector 62 generates injector pulses which are fed to the electron gun 54 in the accelerator 52 for generating electron beam 50. The electron beam 50 is accelerated and guided by the wave guide 56. For this purpose, a high frequency source (not shown) is provided, which supplies radio frequency signals for the generation of an electromagnetic field supplied to the wave guide 56. The electrons injected by the injector 62 and emitted by the electron gun 54 are accelerated by the electromagnetic field in the wave guide 56 and exit at the end opposite the electron gun 54 to form electron beam 50. The electron beam 50 then enters the guide magnet 58 and from there is guided through a window 64 along axis R. After passing through a scattering foil 66 for electron mode (or target for photon mode), the beam 50 passes through a passageway 68 of a shield block 70 and encounters a secondary scattering foil 72 for electron mode (or flattening filter for photon mode). The beam next passes through a measuring chamber 74 in which the dose is ascertained.

Figure 3:
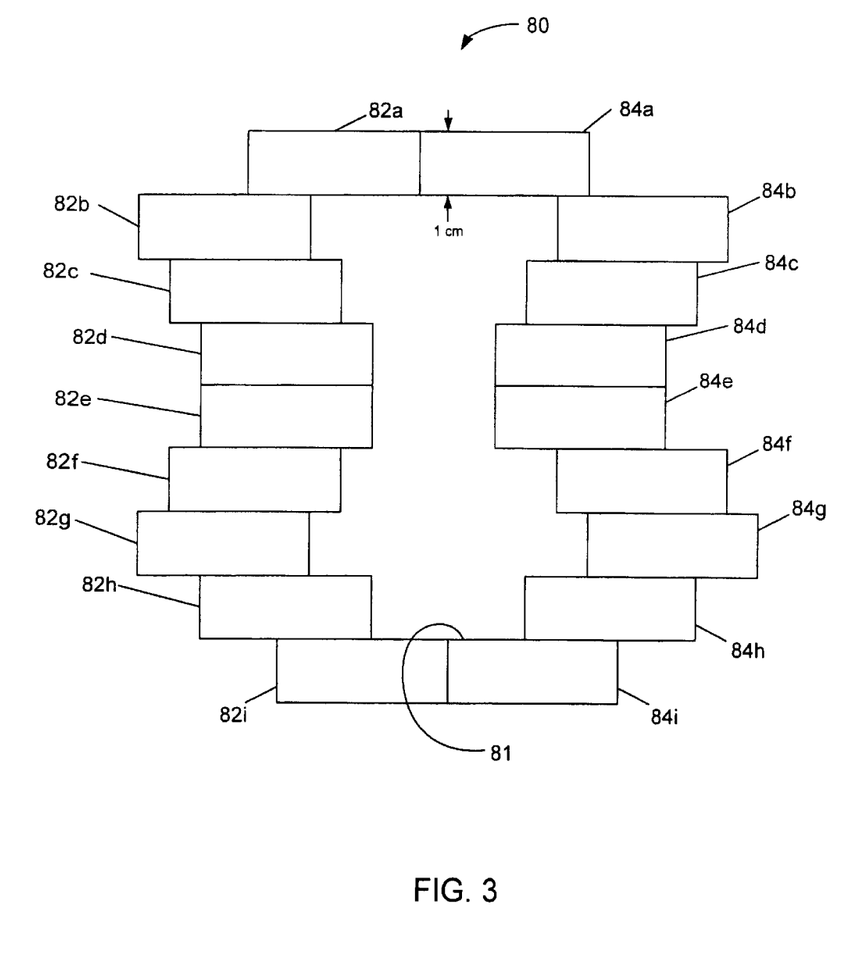
FIG. 3 is a schematic illustrating leaves of a multi-leaf collimator positioned for treatment in the radiation treatment device of FIG. 1.

A beam shielding device, generally indicated at 80, is provided in the path of the beam 50 to define a radiation field 81 (FIGS. 2 and 3). The beam shielding device 80 includes a plurality of opposing plates or leaves 82a–i and 84a–i, only two of which are shown in FIG. 2 for simplification. FIG. 3 illustrates leaves 82a–i and 84a–i (forming leaf pairs 82a and 84a, 82b and 84b, . . . , 82i and 84i) of a multi-leaf collimator mounted between the radiation source and patient and positioned to define a treatment field by delimiting the electron beam 50. The leaves 82a–i, 84a–i typically have a one centimeter width and are substantially impervious to the emitted radiation so that they block healthy tissue from the radiation.

The leaves 82a–i, 84a–i are movable in a direction generally perpendicular to axis R by a drive unit 86 (which is shown in FIG. 2 only with respect to plate 82a) to change the size of the irradiated field so that the distribution of radiation over the field does not need to be uniform (i.e., one region may be exposed to a higher dose than another region). The drive unit 86 includes an electric motor which is coupled to the plate 82a and controlled by a motor controller 90. Position sensors 92, 94 are also coupled to plates 82a, 84a, respectively, for sensing their positions. The drive unit 86 drives the plate 82a in and out of the treatment field, thus creating the desired field shapes.

The motor controller 90 is coupled to a dose control unit 96 which includes a dosimetry controller coupled to the central processing unit 28 for providing set values for the radiation beam for achieving given isodose curves (FIG. 2). The output of the radiation beam is measured by the measuring chamber 74. In response to the deviation between the set values and the actual values, the dose control unit 96 supplies signals to the trigger system 60 which change in a known manner the pulse repetition frequency so that the deviation between the set values and the actual values of the radiation beam output is minimized. The dose absorbed by the patient is dependent upon movement of the collimator plates 82a, 84a. The central processing unit 28 controls execution of the program and the opening and closing of the collimator plates 82a, 84a to deliver radiation according to a desired intensity profile. The central processing unit 28 may include other features described in U.S. Pat. No. 5,724,403, which is incorporated herein by reference in its entirety, for example.

It is to be understood that the radiation treatment device may be different than the one described and shown herein without departing from the scope of the invention. The treatment device 20 described above is provided as an example of a device for use in delivering a treatment developed by the optimization process described below.

As shown in FIG. 1, the gantry 36 is rotatable about axis A over a treatment area on the patient P. Radiation may be delivered, for example, with the gantry 36 in three different positions (A, B, and C) as shown schematically in FIG. 4. Each position of the gantry defines a port between the collimator and treatment area through which the radiation is delivered. For example, if the collimator rotates in a clockwise direction, the collimator is first positioned at port A, then port B, and finally at port C. Port A and port B are adjacent ports, as are ports B and C. Port A may be referred to as a previous port to port B, and port C is a subsequent port relative to port B. In addition to varying the location of the collimator, the leaves of the collimator may be repositioned to define a number of different treatment fields for each port. In conventional intensity modulation radiation therapy, no consideration is given to the sequencing of treatment fields between ports and within the ports. The following describes a method for minimizing leaf travel within each port and between ports by rearranging the order of the treatment fields applied within each port.

Figure 4:
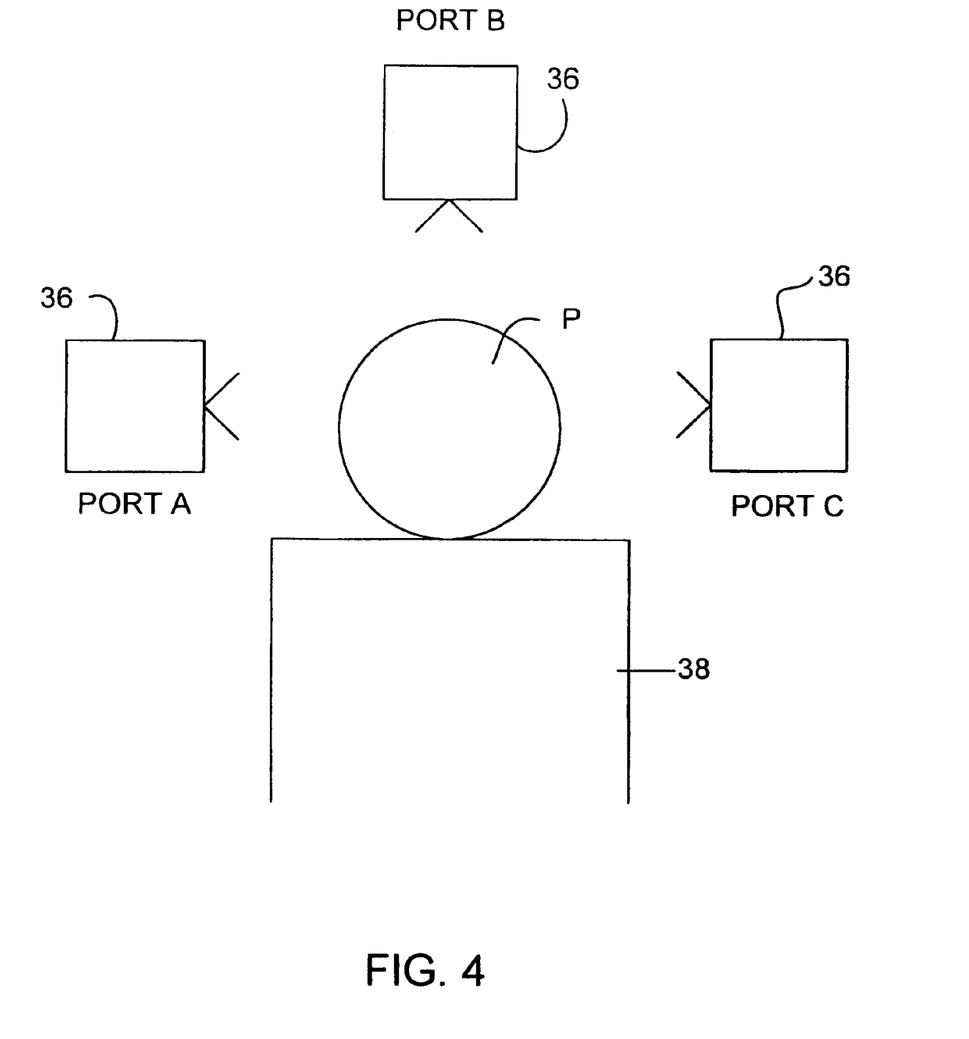
FIG. 4 is a front view of the radiation treatment device illustrating the collimator in three different positions relative to a treatment area on the patient to define three collimator ports.
Figure 5:
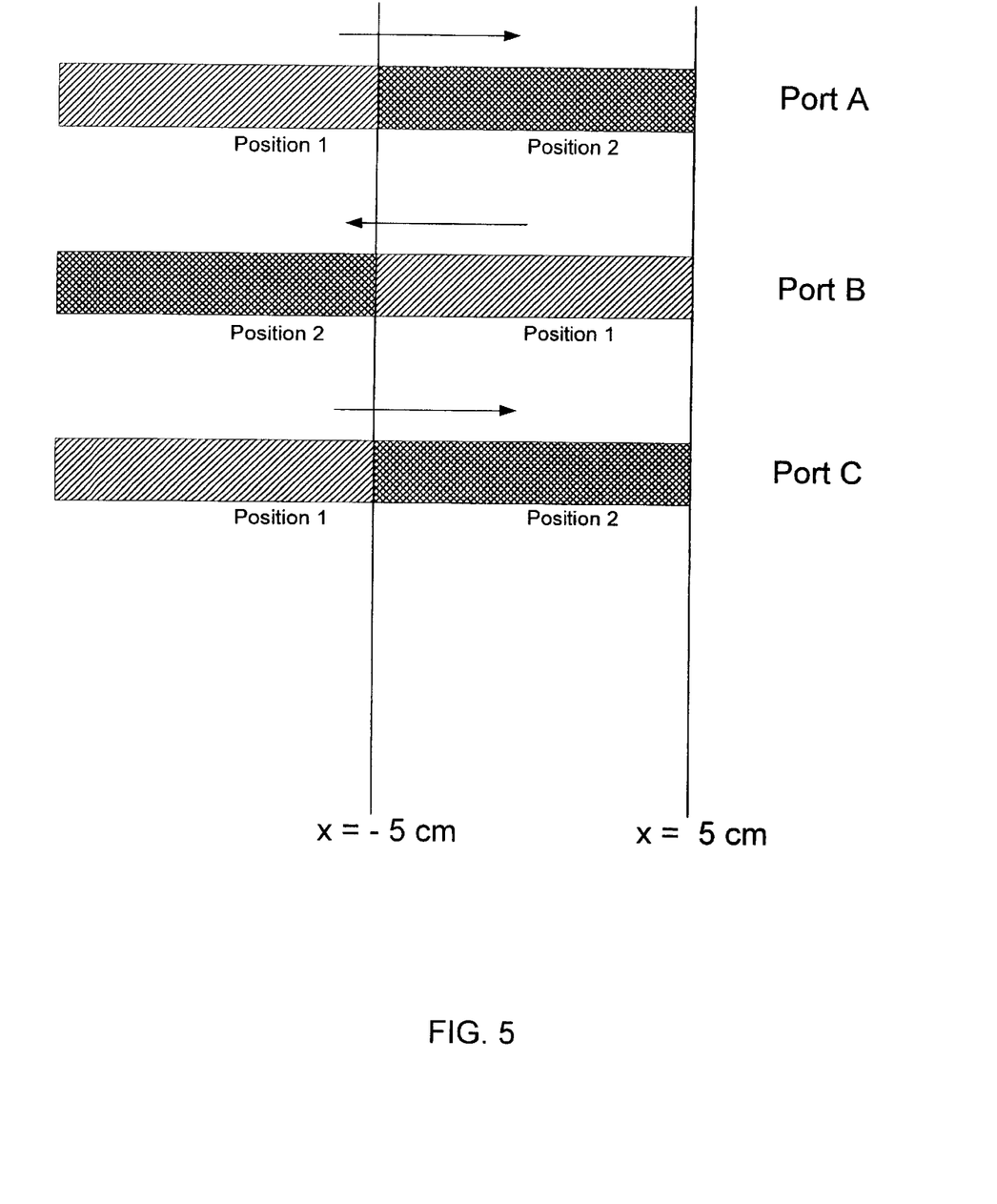
FIG. 5 is a schematic illustrating leaf positions for a sequence of treatment fields for three collimator ports treating generally the same region of a treatment area.

FIG. 5 illustrates exemplary leaf positions for radiation treatment at three ports (A, B, C shown in FIG. 4) where the leaves are positioned to treat generally the same size treatment area (e.g., 10 cm×10 cm area centered about an isocenter) for each port. For simplification only one leaf is shown in FIG. 5. At port A, the leaf is first positioned all the way to the left (as viewed in FIG. 5) at x=−5 cm for the first treatment field. The leaf is then moved so that its leading edge is positioned at x=5 cm to deliver radiation to the second treatment field at port A. After radiation is delivered to the first two treatment fields, the collimator is rotated to position B to deliver radiation at port B. Radiation is first delivered to the treatment field having the leaf positioned at x=5 cm to deliver radiation to the third treatment field. The leaf is then moved to x=−5 cm to deliver radiation to a fourth treatment field at port B. At port C, radiation is first delivered with the leaf positioned with its leading edge at x=−5 cm and then delivered with the leaf positioned at x=5 cm. Since the leaves are already at their starting point at the beginning of each port, leaf travel is reduced as compared to conventional radiation delivery where the leaves are moved back to their starting position at x=−5 cm when the collimator is rotated to a new port position.

While the process described above works well if the ports cover generally the same region of the treatment area, a different process is required if the ports treat areas having different shapes, sizes, or locations. For example, two ports may treat areas that are on opposite sides of a central axis and do not overlap one another (e.g., one field extends from x=−10 cm to −5 cm and the other field extends from x=5 to 10 cm). In this case, the choice for a starting point for a given port depends on the endpoint of the previous port. The sequencing within the port will then depend upon the starting point within the port.

The sequencing may either be performed independently for each port and then reviewed based on treatment fields within adjacent ports, or the fields may be sequenced at a first port and then sequenced at each subsequent port based on the last treatment field in the previous port. The first method (sequencing ports independently) is preferably performed if the user wants to optimize the total treatment time without regard to the total leaf travel. The second method (sequencing ports in order) is preferably performed if the user is more concerned with increasing the life of the multi-leaf collimator than reducing the total treatment time, since the time for leaf travel between ports is hidden in the time for gantry rotation, couch rotation and collimator rotation. Both methods are described below.

For the first method, the treatment fields for each port are sequenced to reduce leaf travel between fields. The sequence for each port is then compared with the last treatment field of the previous port and/or the first treatment field of the subsequent port. For example, if the port only has a previous port (i.e., it is the last port in the treatment) only the last field of the previous port is compared with the first and last fields of the current port. If the leaf positions for the last treatment field of the current port is closer to the leaf positions for the last field of the previous port, then the current port is delivered in reverse order. If the leaf positions for the first treatment field of the current port is closer to the leaf positions of the last treatment field of the previous port, then the current port is delivered in the forward order. Thus, the treatment fields may either be delivered in the sequence selected or the order may be reversed depending on which order provides the minimum leaf travel between adjacent ports.

In the second method, the sequencing for each port is not done until the sequencing of the previous port is completed. In this case, the last treatment field of the previous port is used to select the first treatment field for the current port so that the leaf travel between adjacent ports is minimized. The sequence for the remaining treatment fields within the port is then selected. Hence, the sequence in the port may not necessarily be the optimum one, since the first treatment field cannot be changed. This process is continued until all ports have been sequenced.

Both of the methods described above may be performed and the results compared so that the user can select the optimum sequencing. In the case where one method reduces both the treatment time and the total leaf travel time, this sequence is selected. A merit function that selectively weighs the treatment time versus the total leaf travel time may be used, and the optimization may also involve changing the starting and end point for all ports (i.e., optimization method simultaneously considers all ports rather than doing each port independently or sequentially).

If only a small number of ports are used and each port only has one or two treatment fields, it will be possible to select the optimum sequence of treatment fields while considering the treatment fields in adjacent ports by drawing each possible sequence and rearranging the sequences until leaf travel is minimized. However, as the number of fields or ports increases, a more efficient method is required. One possible method is to use graph theory to select a sequence of treatment fields. In order to use graph theory, the leaf positions for each treatment field are considered vertices and the distance between adjacent fields are represented by edges. Each port is thus a collection of vertices and edges. Each edge has a length which represents the amount of leaf travel in going from one leaf position for a treatment field at the first vertex of this edge to another leaf position at another treatment field at the second vertex of this edge. The constraint on the graph is that each vertex must be visited once (i.e., radiation must be delivered to all treatment fields). In order to reduce leaf travel within the port, the shortest path that contains all vertices is found. This may be done by using methods to solve a Hamiltonian cycle problem, also known by those skilled in the art as the traveling salesman problem (see e.g., Algorithms in C++, Robert Sedgewick, Addison Wesley, 1992; Press, Teukolsky, Flannery and Vetterling, Numerical Recipes in C). Once the cycle has been determined, the edge that has the longest length in the cycle is identified. The vertices connected to that edge then become the starting point and the ending point. This provides the shortest path connecting all vertices one time.

An example of an approximate algorithm to solve the Hamiltonian cycle involves selecting a vertex that is at a farthest left edge of the graph as the starting point. Of the remaining vertices, the shortest one with an edge at the starting point is selected. This new vertex is now a new starting point and the process of searching for the next nearest vertex among the remaining one continues. This iterative process continues until all the vertices have been selected. The last vertex is then connected to the first vertex chosen to complete the cycle. This process may not necessarily provide the best result, however, it is quicker than a search for all possible sequences. For three vertices (i.e., three treatment fields), this process does yield the best result. For other types of segments, this shortened process may be used where several iterations of sequencing is necessary. For example, this process may be used to evaluate how quickly a particular set of treatment fields can be delivered so that the set of treatment fields with the minimum time may be selected. Once a final set of treatment fields is selected, a more rigorous algorithm, such as simulated annealing, may be used to sequence the treatment fields (see, e.g., "Numerical Recipes in C" by Vetterling, Press, Flannery, and Teukolsky, 1992, Cambridge University Press). Another method that looks at the initial sequence of fields for parts of the sequence that are particularly long, may also be used. The problem treatment field is then replaced with a field earlier in the sequence that reduces the leaf travel time for that link in the sequence. The problem treatment field can then be inserted somewhere in the sequence such that the total time is minimized. Several iterations of this process may be performed until the travel time cannot be further decreased.

Figure 6:
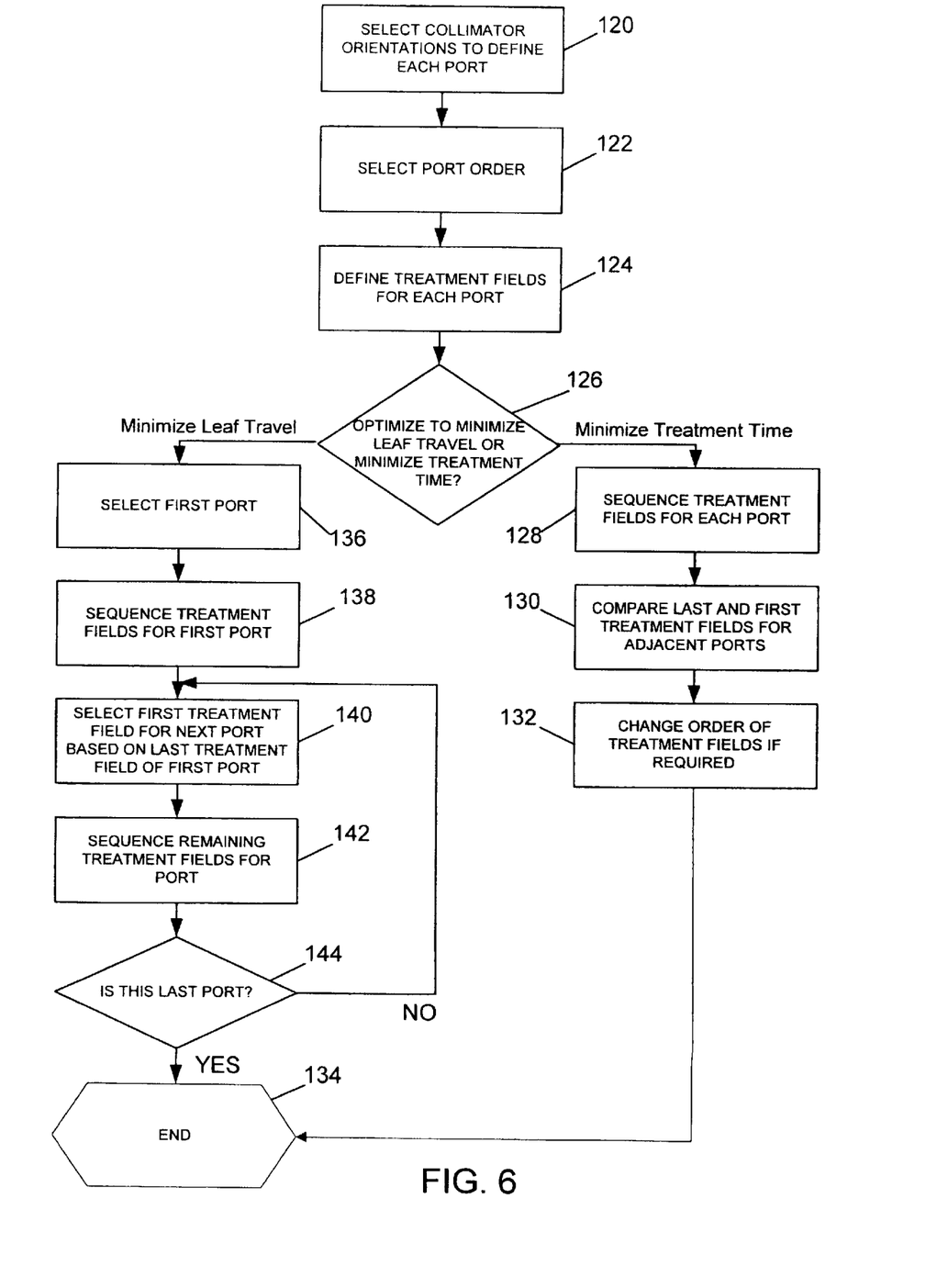
FIG. 6 is a flowchart illustrating a process for sequencing treatment fields for radiation treatment with a multi-leaf collimator.

FIG. 6 is a flowchart illustrating a process for sequencing treatment fields for radiation delivery with a multi-leaf collimator. The collimator port positions are first defined and ordered based on the direction of travel of the collimator (steps 120 and 122). For example, as shown in FIG. 4, the collimator travels clockwise so that the collimator is positioned for port A first, then port B, and finally port C. The collimator may also travel counterclockwise, or the collimator may be rotated first clockwise and then counterclockwise. The treatment fields are defined for each of the ports at step 124. A decision is made whether to optimize the radiation treatment to reduce total treatment time or the amount of leaf travel (step 126). If the treatment is optimized to reduce total treatment time, the treatment fields within each port are individually sequenced to minimize leaf travel between fields (step 128). The first and last treatment fields of each port are then compared with the first and last treatment fields of adjacent ports (step 130). The sequence of treatment fields within one or more ports are reversed if required to reduce leaf travel between ports (step 132).

If the treatment is optimized to minimize leaf travel one of the ports is selected as the first port. The starting port may be selected near the limiting position capability of the gantry, for example. The treatment fields are sequenced for this first port to reduce the amount of leaf travel between treatment fields (step 138). The first treatment field for the next port is selected to minimize leaf travel between the last treatment field of the previous port and the first treatment field of the adjacent port (step 140). The remaining treatment fields for the port are then sequenced based on the selected first treatment field for that port (step 142). If this is the last port, the process is complete (step 134), if there are more ports, the process continues.

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A method for sequencing treatment fields defined by leaves of a multi-leaf collimator positioned to block radiation from a radiation source and define an opening between the radiation source and a treatment area, the multi-leaf collimator operable to rotate relative to said treatment area to define a plurality of treatment ports, each of said ports having at least one treatment field, the method comprising ordering the collimator ports based on direction of travel of the collimator relative to said treatment area such that each port has at least one corresponding adjacent port, and selecting a sequence of said treatment fields for each collimator port based on said treatment fields within adjacent ports to optimize delivery of radiation.

2. The method of claim 1 wherein selecting a sequence of treatment fields comprises selecting a sequence of treatment fields resulting in a shortest total radiation treatment time.

3. The method of claim 1 wherein selecting a sequence of treatment fields comprises selecting a sequence of treatment fields resulting in minimum overall leaf travel from one treatment field to the next.

4. The method of claim 1 wherein selecting a sequence of treatment fields comprises selecting a sequence of treatment fields independently for each collimator port, and modifying an order of the treatment fields for one or more of the ports based on a last treatment field of a previous port or a first treatment field of a subsequent port.

5. The method of claim 4 wherein modifying an order of the treatment fields comprises reversing an order of the treatment fields within one of said ports.

6. The method of claim 1 wherein selecting a sequence of treatment fields comprises selecting a sequence of treatment fields for a first port and selecting a first treatment field for a subsequent port that requires the least amount of travel from a last treatment field of a previous port.

7. The method of claim 6 further comprising selecting a sequence for remaining treatment fields of the subsequent port.

8. The method of claim 6 further comprising repeating selecting a sequence of treatment fields until the treatment fields within each of said ports is sequenced.

9. The method of claim 1 wherein selecting a sequence of treatment fields comprises utilizing graph theory.

10. A method for sequencing treatment fields defined by leaves of a multi-leaf collimator positioned to block radiation from a radiation source and define an opening between the radiation source and a treatment area, the multi-leaf collimator operable to rotate relative to said treatment area to define a plurality of treatment ports, each of said ports having at least one treatment field, said treatment fields of each of said ports configured to treat generally the same region on said treatment area, ordering the collimator ports based on direction of travel of the collimator relative to said treatment area such that each port has at least one corresponding adjacent port, and selecting a sequence of treatment fields for each collimator port such that the leaves are moved in opposite longitudinal directions within adjacent ports to optimize delivery of radiation.

11. A system for delivering radiation to a treatment area from a radiation source, the system comprising:

a collimator having multiple leaves for blocking radiation from said source and defining an opening between the radiation source and said treatment area, the collimator operable to rotate relative to said treatment area to define a plurality of treatment ports, each of said ports having at least one treatment field defined by a position of the leaves; and a processor for selecting a sequence of treatment fields for each collimator port to optimize delivery of radiation.

12. The method of claim 11 wherein the processor is operable to select a sequence of treatment fields resulting in a shortest total radiation treatment time.

13. The method of claim 11 wherein the processor is operable to select a sequence of treatment fields resulting in minimum leaf travel from one treatment field to the next.

14. The method of claim 11 wherein the processor is operable to select a sequence of treatment fields independently for each collimator port, and modify an order of the treatment fields for one or more of the ports based a last treatment field of a previous port or a first treatment field of a subsequent port.

15. The method of claim 11 wherein the processor is operable to select a sequence of treatment fields for a first port and selecting a first treatment field for a subsequent port that requires the least amount of travel from a last treatment field of a previous port.

* * * * *